(12) United States Patent
Grad et al.

(10) Patent No.: US 8,707,462 B2
(45) Date of Patent: *Apr. 29, 2014

(54) HINGED EYE SHIELD

(71) Applicant: TIDI Products, LLC, Neenah, WI (US)

(72) Inventors: Michael Grad, Carlsbad, CA (US); Gad Shaanan, La Jolla, CA (US)

(73) Assignee: TIDI Products, LLC, Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/915,240

(22) Filed: Jun. 11, 2013

(65) Prior Publication Data

US 2013/0276216 A1    Oct. 24, 2013

Related U.S. Application Data

(63) Continuation of application No. 13/545,506, filed on Jul. 10, 2012, now Pat. No. 8,458,813, which is a continuation of application No. 12/360,031, filed on Jan. 26, 2009, now Pat. No. 8,214,921.

(60) Provisional application No. 61/024,533, filed on Jan. 29, 2008, provisional application No. 61/115,880, filed on Nov. 18, 2008.

(51) Int. Cl.
| | |
|---|---|
| A41D 13/11 | (2006.01) |
| A61F 9/04 | (2006.01) |
| A61F 9/02 | (2006.01) |
| A42B 3/20 | (2006.01) |
| G02C 5/22 | (2006.01) |
| A61F 9/00 | (2006.01) |
| A63B 71/10 | (2006.01) |

(52) U.S. Cl.
CPC ............. *A42B 3/20* (2013.01); *G02C 5/2218* (2013.01); *G02C 5/2272* (2013.01); *A63B 71/10* (2013.01)
USPC ............................ 2/9; 2/11; 2/12; 2/13; 2/15

(58) Field of Classification Search
CPC .......... A42B 3/20; A42B 3/223; A42B 3/222; A63B 71/10; A61F 9/02; A61F 9/025; G02C 3/003; G02C 3/02; G02C 5/006; G02C 5/22; G02C 5/2218; G02C 5/2272
See application file for complete search history.

(56) References Cited

U.S. PATENT DOCUMENTS

| | | |
|---|---|---|
| 3,787,113 A | 1/1974 | Shedrow |
| 4,190,333 A | 2/1980 | Lambert |

(Continued)

FOREIGN PATENT DOCUMENTS

| | | |
|---|---|---|
| KR | 20000003265 | 1/2000 |
| WO | WO8900844 | 2/1989 |
| WO | WO2005026623 | 3/2005 |

OTHER PUBLICATIONS

International Search Report PCT/US2009/032031 dated Sep. 8, 2009; pp. 1-3.

*Primary Examiner* — Bobby Muromoto, Jr.
(74) *Attorney, Agent, or Firm* — Boyle Fredrickson, S.C.

(57) ABSTRACT

An eye shield is provided that may allow for compact storage and ease of assembly and use. The eye shield may include a frame for supporting the eye shield upon a user and a hinge arranged upon a forehead portion of the frame. A flexible lens may be mounted to the hinge and arranged to move from a flat position by pivoting about the hinge to conform to a shape of the frame.

7 Claims, 13 Drawing Sheets

(56) References Cited

U.S. PATENT DOCUMENTS

| | | |
|---|---|---|
| 4,391,498 A | 7/1983 | Rengstorff |
| 4,451,127 A | 5/1984 | Moffitt |
| 4,523,819 A | 6/1985 | Dianitsch et al. |
| 4,610,036 A | 9/1986 | LaPrairie |
| 4,741,611 A | 5/1988 | Burns |
| 4,868,930 A | 9/1989 | Blackstone |
| 5,129,102 A | 7/1992 | Solo |
| 5,297,298 A | 3/1994 | Salatka et al. |
| 5,402,552 A | 4/1995 | Chen |
| 5,446,925 A | 9/1995 | Baker et al. |
| 5,500,694 A | 3/1996 | Roever et al. |
| 5,519,896 A | 5/1996 | Ford |
| 5,576,776 A | 11/1996 | Schneller |
| 5,652,954 A | 8/1997 | Paiement et al. |
| 5,815,235 A | 9/1998 | Runckel |
| 5,929,966 A | 7/1999 | Conner |
| 5,956,117 A | 9/1999 | Suh et al. |
| 6,010,215 A | 1/2000 | Miceli |
| 6,024,446 A | 2/2000 | Hall et al. |
| 6,247,811 B1 | 6/2001 | Rhoades et al. |
| 6,308,711 B1 | 10/2001 | Goldberg |
| 6,718,561 B2 | 4/2004 | Dondero |
| 6,783,236 B2 | 8/2004 | Chou |
| 6,935,741 B2 | 8/2005 | Denney |
| 6,948,812 B2 | 9/2005 | Wichner |
| 6,959,989 B2 | 11/2005 | Holm |
| 6,964,067 B1 | 11/2005 | Hartman |
| 7,029,114 B2 | 4/2006 | Smith |
| 7,039,959 B2 | 5/2006 | Dondero |
| 7,058,991 B2 | 6/2006 | Hartman et al. |
| 7,188,625 B2 | 3/2007 | Durette |
| 7,712,894 B2 | 5/2010 | Tsai |
| 7,921,468 B2 | 4/2011 | Sutton |
| 8,214,921 B2 * | 7/2012 | Grad et al. ............... 2/9 |
| 8,458,813 B2 * | 6/2013 | Grad et al. ............... 2/9 |
| 2002/0071088 A1 | 6/2002 | Cardenas |
| 2004/0141148 A1 | 7/2004 | Chou |
| 2005/0039240 A1 | 2/2005 | Kidouchim |
| 2005/0052610 A1 | 3/2005 | Denney |
| 2005/0052612 A1 | 3/2005 | Kidouchim |
| 2005/0174532 A1 | 8/2005 | Wichner |
| 2005/0268384 A1 | 12/2005 | Hartman |
| 2005/0268385 A1 | 12/2005 | Hartman et al. |
| 2006/0017880 A1 | 1/2006 | Smith |
| 2006/0050224 A1 | 3/2006 | Smith |
| 2006/0106401 A1 | 5/2006 | Deutschmann et al. |
| 2006/0176441 A1 | 8/2006 | Katz et al. |
| 2006/0243286 A1 | 11/2006 | Durette |
| 2006/0256278 A1 | 11/2006 | Amioka |
| 2007/0211208 A1 | 9/2007 | Cunningham et al. |
| 2007/0252944 A1 | 11/2007 | Welchel et al. |
| 2007/0279583 A1 | 12/2007 | Bovee |
| 2009/0073376 A1 | 3/2009 | Swift |
| 2009/0279047 A1 | 11/2009 | Tsai |
| 2009/0307817 A1 | 12/2009 | Stachler et al. |
| 2009/0316106 A1 | 12/2009 | Kitayama |
| 2010/0073625 A1 | 3/2010 | Engstrom |
| 2010/0253903 A1 | 10/2010 | Weston |

* cited by examiner

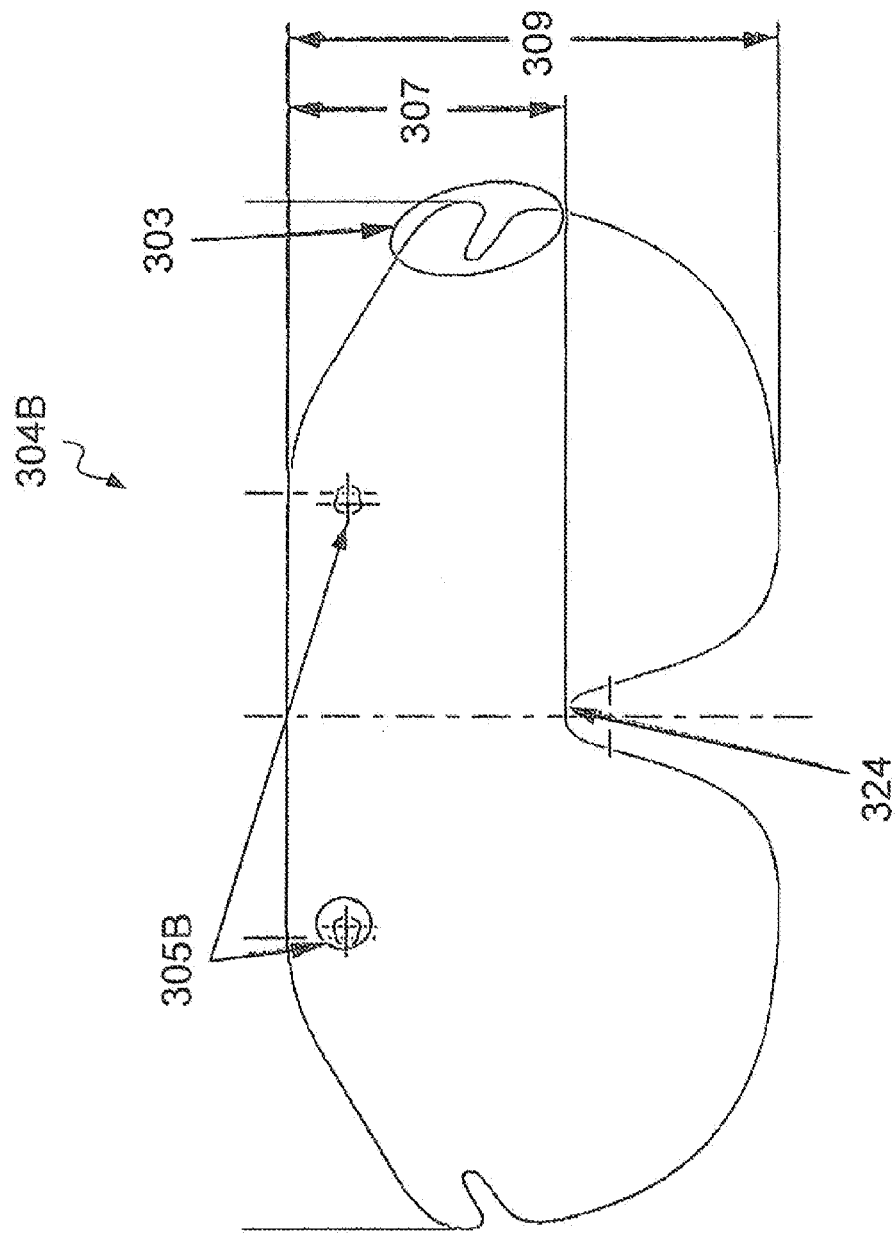

HINGED EYE SHIELD

CROSS REFERENCE TO RELATED APPLICATIONS

The present patent application is a continuation of application Ser. No. 13/545,506 filed on Jun. 11, 2013 which is a continuation of application Ser. No. 12/360,031 filed on Jan. 26, 2009, now U.S. Pat. No. 8,214,921, which claims priority to Application No. 61/024,533 filed on Jan. 29, 2008 and Application No. 61/115,880 filed on Nov. 18, 2008, all of which are incorporated by reference herein, in their entireties.

BACKGROUND

Protective eyewear usually covers the eye area in order to prevent particulates, infectious fluids, or chemicals, or light and other harmful rays such as ultraviolet (UV) radiation, lasers, and so on from striking the eyes. Commonly referred to as eye shields, protective eyewear comes in a variety of forms such as goggles, masks, glasses, et cetera and is useful in a number of different activities to protect a user's eyes from harm. For example, protective eyewear is especially useful for splash protection in health and safety-related environments where the user's eyes may be exposed to chemicals, blood-borne pathogens or other potentially infectious materials (OPIM). Protective eyewear may also be used by workers in a construction zone to prevent harmful debris or other particles or materials from striking workers' eyes. Protective eye wear is also important in sports and other outdoor activities like bicycling, running or sunbathing where a user's eyes may need protection from wind, dust or other air-born debris or from harmful light and ultraviolet (UV) rays.

Protective eyewear can be very expensive depending on the application. For example, cyclists use very expensive protective eyewear to protect their eyes from wind, sunlight and from dust and other debris striking a user's eyes at high speeds. A cyclist's protective eyewear can become damaged, lost or stolen and often has to be replaced on a regular basis, which can lead to significant expense due to the replacement value of the protective eyewear. Additionally, in certain industries eye shields may become contaminated or otherwise damaged after every use, which can lead to significant expense for eye shields with high replacement value. For example, eye shields used in a laboratory or emergency room environment may become contaminated due to exposure or potential exposure to OPIM.

As a result, certain eye shields are designed to be disposable after a single use. Disposable eye shields are useful in these cases since an eye shield may become contaminated or damaged during use and replacing the eye shield can be more cost-effective or practical than sterilizing a contaminated eye shield or repairing a damaged eye shield. In many cases it is safer and more time and cost efficient to simply discard the eye shields after use rather than attempt to disinfect or otherwise decontaminate them. Additionally, regulations may require protective eyewear to be disposable after a single use. For example, in an operating room environment it may be required by government regulations for users to dispose of their protective eyewear following surgery or other medical procedure.

Eye shields on the market today are also fairly cumbersome and difficult to store due to having a relatively large profile. These eye shields usually consist of a static, right-angle lens and frame design which can be cumbersome to carry around when not in use and must be stored in specially designed cases that are also quite cumbersome based on their larger profiles. These eye shields may be designed to be folded and stored in a case and require cleaning or wiping to keep the lens area clean. Additionally, packaging and transporting eye shields to the point of sale can be very difficult because of their cumbersome profile in the static, right-angle lens and frame design. For example, eye shields for use in a laboratory or medical-related environments are often packaged and sold in a preassembled configuration so that they may be easily used right out of the package. However, preassembled eye shields are often cumbersome to store and transport because they are packaged and shipped in the preassembled configuration which requires a large amount of space in their storage and/or shipping containers. These containers may only store a limited number of disposable eye shields. In addition these containers may require more space than is practically available at the eye shield's point-of-use, such as in a medical treatment room.

SUMMARY

At least certain embodiments describe an apparatus comprising a flip-to-wear eye shield designed for efficient storage and ease of use, the eye shield dispensed in a compact, easy-to-assemble configuration, the eye shield including a protective lens and a frame coupled with the protective lens by one or more hinges, the one or more hinges configured to allow the protective lens to pivot with respect to the frame from a first substantially flat position for compact storage to a second position ready for use.

BRIEF DESCRIPTION OF THE DRAWINGS

FIG. 3B illustrates a lens for a flip-to-wear eye shield according to the alternate embodiment of the invention.

DETAILED DESCRIPTION

To maximize convenience for the user, a disposable eye shield should be easy to store and dispense and should require minimal effort to assemble. At least certain embodiments describe a flip-to-wear eye shield designed for efficient storage, convenient dispensing, and ease of assembly and use with minimal user effort. Such an embodiment includes a protective lens to protect the user's eyes and a frame coupled with the protective lens by one or more hinges to allow the protective lens to pivot with respect to the frame from a substantially flat position for easy storage and into a fully assembled position ready for wearing and use.

Figure 1:
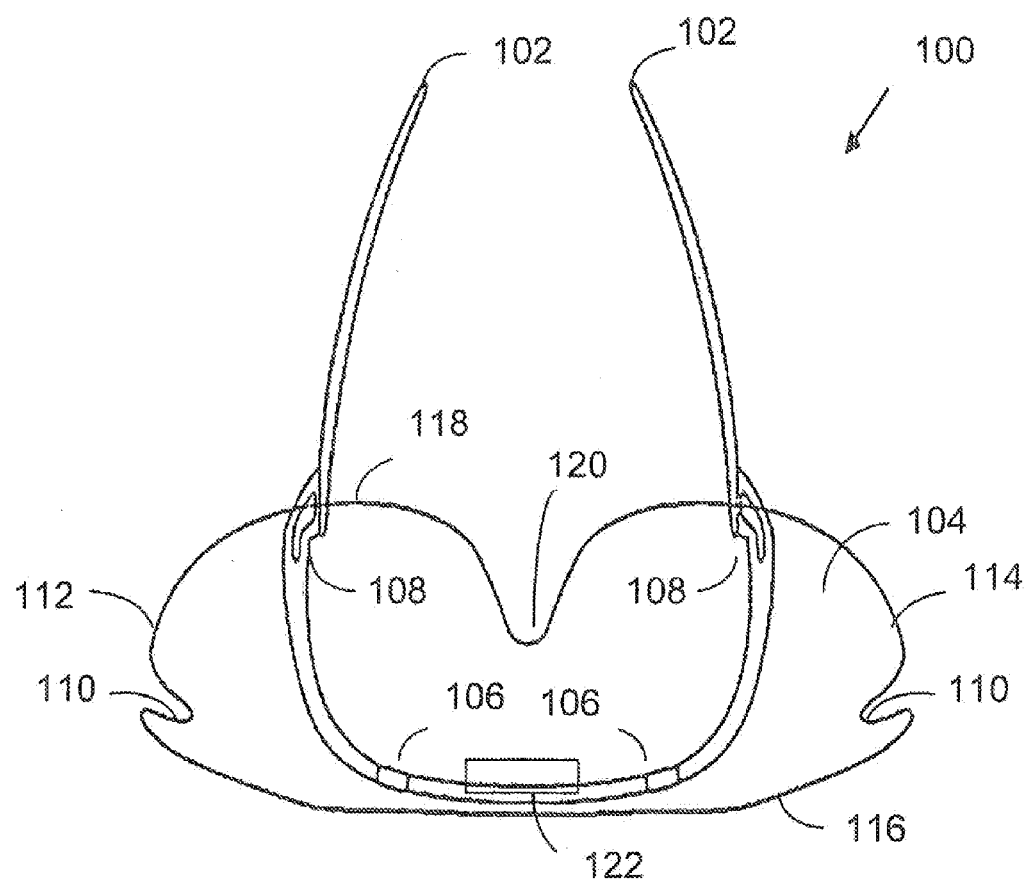
FIG. 1 illustrates a flip-to-wear eye shield in a substantially flat position designed for easy storage and dispensing according to an exemplary embodiment of the invention.

FIG. 1 illustrates a flip-to-wear eye shield in a substantially flat position designed for easy storage and dispensing according to an exemplary embodiment of the invention. In the illustrated embodiment, eye shield 100 includes a frame 102, a lens (or other eye covering member) 104, and a pair of hinges 106 that connects the frame 102 to the lens 104 allowing the lens 104 to pivot up and down with respect to the frame 102. Although a pair of hinges 106 is shown in FIG. 1, any number of hinges (including a single hinge) is contemplated within the teachings of this description. Additionally, the hinge may be a separate device, built-into part of the frame, built-into part of the lens, or any combination thereof. For example, the lens may have built-in hooks that engage and fit around respective parts of the frame in a hinge-like configuration allowing the lens to pivot with respect to the frame. Likewise, the frame may have built-in hooks that engage and fit around respective parts of the lens in a hinge-like configuration allowing the frame to pivot with respect to the lens. In a preferred embodiment, a pair of hinges 106 is used preferably where each hinge is directly above the user's eyes. In one embodiment, the hinges 106 clip onto the frame 102.

In FIG. 1 the eye shield 100 is shown in a substantially flat position. Eye shield 100 may be pivoted from the substantially flat position to a fully assembled position ready for use by pushing the lens 104 down so that it rotates inside the frame 102, pivoting the lens 104 with respect to the frame 102 on the hinges 106 until the notches 110 on the lens 104 are locked into position onto the connective mechanisms 108. In the illustrated embodiment, the connective mechanisms 108 are shown as bends in the frame 102. However, this is given by way of illustration and not of limitation as any connective mechanism is contemplated within the teachings of this description.

In at least certain embodiments, the eye shield 100 may be preassembled with the frame 102, lens 104, and hinges 106 in the substantially flat position. The hinges 106 may be fixed to the frame 102 in a pivoting relationship and connected to the lens 104 by a fastening mechanism such as a nipple and hole connection, a press pin, snap or any other fastening mechanism. One example of the hinges 106 are annular shaped hinges holding onto the frame 102 in a pivoting relationship. However, this is given by way of illustration and not of limitation as any other mechanism that provides the function of pivoting on the frame to change the angular position of the lens 104 relative to the frame 102 is contemplated within the teachings of this description.

In FIG. 1 the lens 104 is substantially transparent and flexible, and preferably made of a thin gauge material. Suitable materials may include polyvinyl chloride, polyethylene, polypropylene, polystyrene, polycarbonate, acetate, cellulosic, or acrylic plastic. The specific material used is not critical although a material which is optical grade, anti-static coated and fog resistant is preferred. A preferred material may include a polycarbonate resin such as commercially available Lexan®, or a thermoplastic carbonate-linked polymer produced by reacting bisphenol-A and phosgene.

However, other plastics, as described above, may also be used, and since, in at least certain embodiments, single use, disposable lenses are intended; less expensive plastics may be quite suitable. A preferred plastic may also be relatively thin and commonly available in flexible sheets from which the lens can be readily stamped or cut, without shattering, cracking, and etc. The lens material is also preferably flexible so that it can be bowed to conform to a users face without significant visual distortion. The lens may also be of a certain length such that, when secured in the frame 102, it extends over the eyes beyond the user's temples, thereby offering significant protection for the user's eyes from both the front and side directions with insignificant or virtually no visual distortion in the area of the bend or bow of the frame 102. Additionally, the lens 104 may be clear, polarized, or it may be treated for UV protection, tinted, smoked, mirrored, or coated for hardness. Lens 104 may also be non-reflective, anti-fogging, and the like. In the illustrated embodiment of FIG. 1 the lens 104 extends between a pair of opposite side edges 112 and 114 which are separated at a distance such that the lens 104 extends as far as the users temples when the eye shield is worn. In this embodiment, the upper edge 116 extends along the user's forehead, usually at or above the eyebrows, with a lower edge 118 extending down as far as the user's cheeks with notch 120 resting on or extending slightly above the bridge of the user's nose. There may also be an optional cushion 122 in the form of an elongated piece or strip comprising foam, plastic, rubber, or preferably a lightweight sponge material having an adhesive along one or more surfaces. Cushion 122 may be used to facilitate user comfort while wearing the eye shield 100, and may be placed along the upper edge 116 of lens 104 so that it offers a pad between the lens 104 and the user's forehead.

Figure 2:
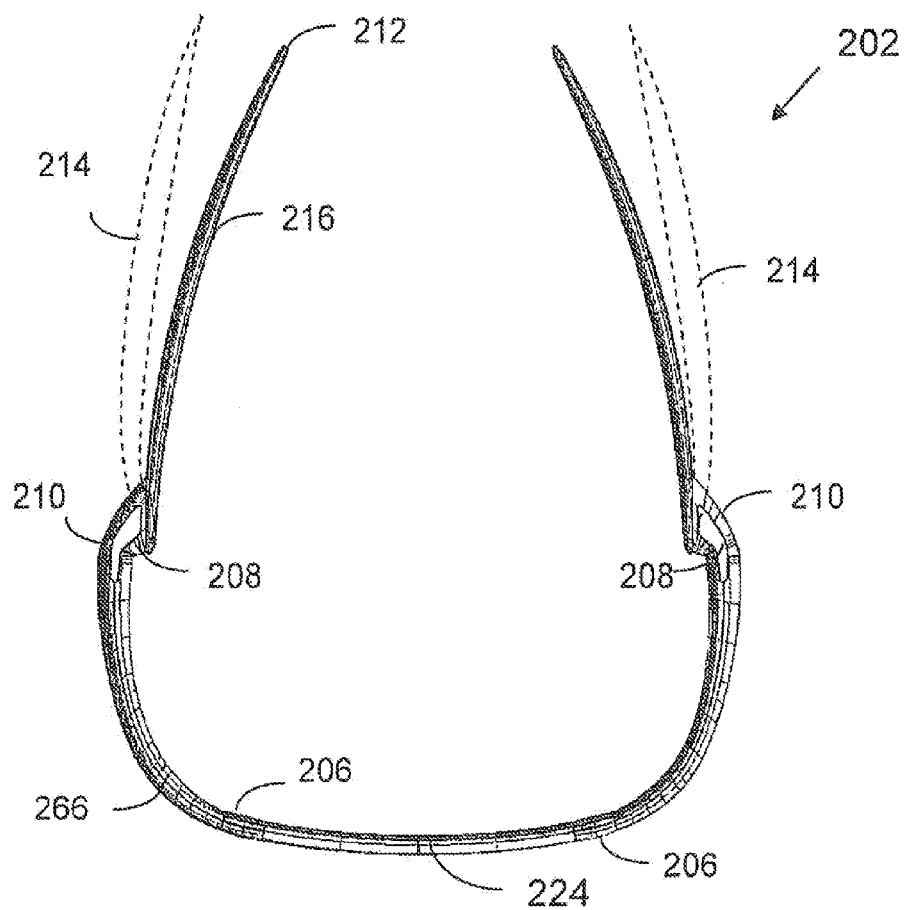
FIG. 2 illustrates a frame of a flip-to-wear eye shield according to an exemplary embodiment of the invention.

FIG. 2 illustrates a frame of a flip-to-wear disposable eye shield according to an exemplary embodiment of the invention. The frame 202 illustrates one embodiment, comprising a plastic, composite, or metal rod or tube preferably made from a spring-like memory retaining material. In the illustrated embodiment, the frame 200 is bowed along its length to form a u-shaped member extending from an area behind the user's ears and along the user's forehead. A forehead portion 224 is shaped to contour to a user's forehead and to bend around a temple area 266 to fit to the user's face. Opposite ends 212 are connected to the temple area 266 of the frame 200 with, for example, inward bends 208. These inward bends 208 are given by way of illustration and not of limitation as any known mechanism may be employed to connect the opposite ends 212 with the temple area 266 of the frame 202. In this embodiment, inward bends 208 are configured to align with the notches of the lens such as notches 110 of lens 104 shown in FIG. 1. The bends 208 align with the notches to provide areas for the notches 110 to be locked into position. Once the notches 110 are locked into the bends 208, the eye shield is in the fully assembled position ready for wearing and use by a user. This locked position prevents the lens 104 from pivoting or otherwise moving on the hinge 206 relative to the frame 200. The frame 200 is preferably of a length sufficient so that its two opposite ends 212 extend slightly beyond a user's ears and rest in the ear saddle when the eye shield is placed on the user's head. Where, as in the illustrated embodiment, a bowed or u-shaped frame is used, the location of the bends (or other connective mechanisms) 208 may be chosen such that bends 208 align with the notches 110 of the lens 104 and lock into position.

Although a rigid frame 200 could be used, the frame 200 is preferably formed of a light-weight, spring-like material such as polyethylene, polypropylene or PVC which retains its memory to a first unsprung position as shown in FIG. 2, and which can be sprung to a second position 214 (shown as dashed lines in FIG. 2) when the frame 200 is placed on a user's head. In this second sprung position, the opposite ends 212 are urged or biased toward the original unsprung position under the influence of the lightweight, spring-like material. Such a feature may assist in securing the frame 200 of eye shield 100 on a user's head as the bowed frame 200 is biased toward the direction of the unsprung position.

Alternatively, the frame 200 may be made of other resilient materials of a similar shape such as metal, or of other suitable plastics having such a feature. The cross-sectional shape of the frame 200 may be varied, such as tubular, solid, flat, oval, or rectangular shape, as long as the aforesaid characteristics and features are present. The second sprung position 214 shown in FIG. 2 may vary in size and shape, depending on the size of the user's head. In one embodiment, where the frame 200 is made from a spring-like plastic, a "living" hinge may be incorporated. Such a living hinge is a thin, flexible, skin-like film portion of the plastic which may be repeatedly folded and integrally formed on the plastic itself. This type of living hinge may be formed along each of the side extensions 216 of the frame 200. Such integrally formed plastic hinges may also be formed on the inside bow of the frame 200 so that they do not interfere with or defeat the biased function of the frame 200 as shown in FIG. 2. Such hinges are well known in the art and offer the advantage of allowing the side extensions 216 inwardly toward the inside of and in the plane of the frame 200.

The disclosed eye shield offers several advantages and a variety of uses over previous eye covering devices. Because the eye shield is so light-weight, it is not as easily displaced or dislodged from the user's head even during exercise or similar activity. The eye shield also provides for easy packaging and storage when in the substantially flat position because of the low-profile the eye shield assumes, and yet it can be easily and readily locked into a position ready to use with minimal effort by a user. For specific applications, the user may choose from a flip-to-wear eye shield with a specific lens, such as clear, tinted, UV protected, polarized, and so on. The eye shield is also easily fitted on the user's head without the need for a fastener and provides a wrap-around, light-weight, distortion free viewing lens which extends substantially beyond the side of the user's eyes offering additional protection from fluids, dust, or other OPIM contacting or impinging on the user's eyes from the side. Such a feature is important, for example, for protecting healthcare professionals and patients from transfer of blood-borne pathogens and OPIM. The eye shield additionally offers protection during recreational use, such as bike riding, running, jogging, as well as in more casual recreational use regardless of the activity of the user.

Figure 3A:
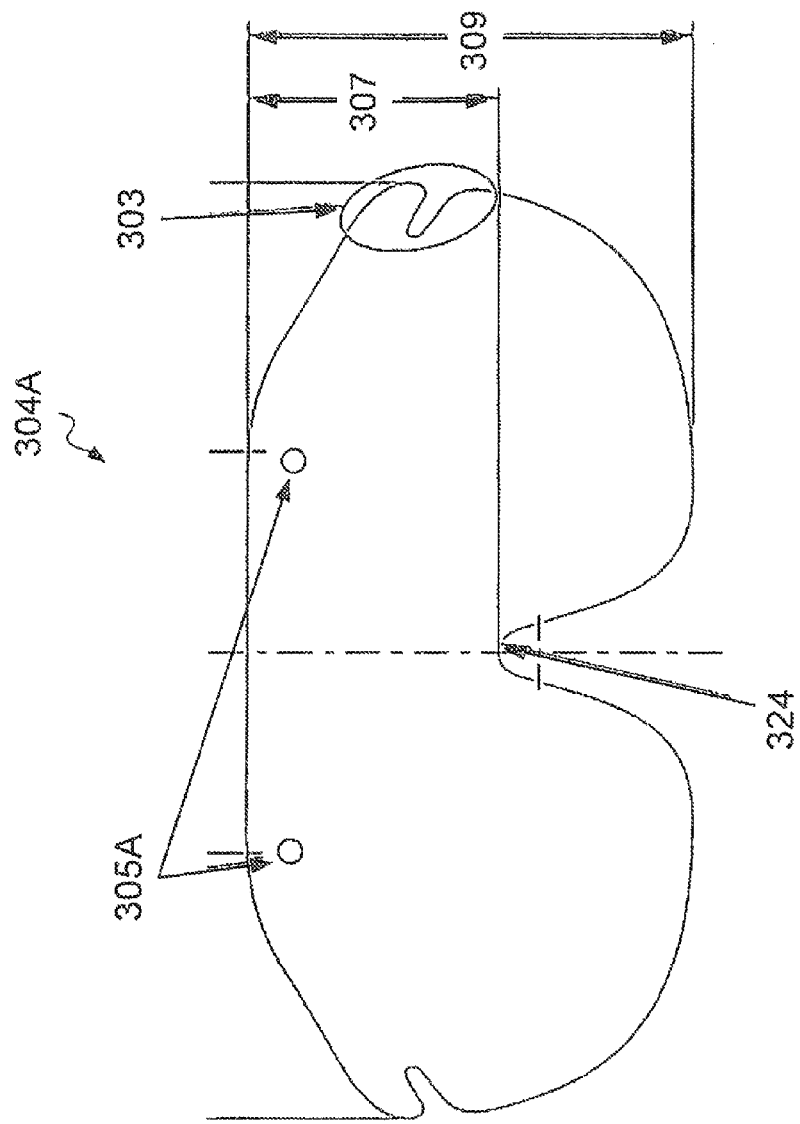
FIG. 3A illustrates a lens for a flip-to-wear eye shield according to an exemplary embodiment of the invention.
Figure 3C:
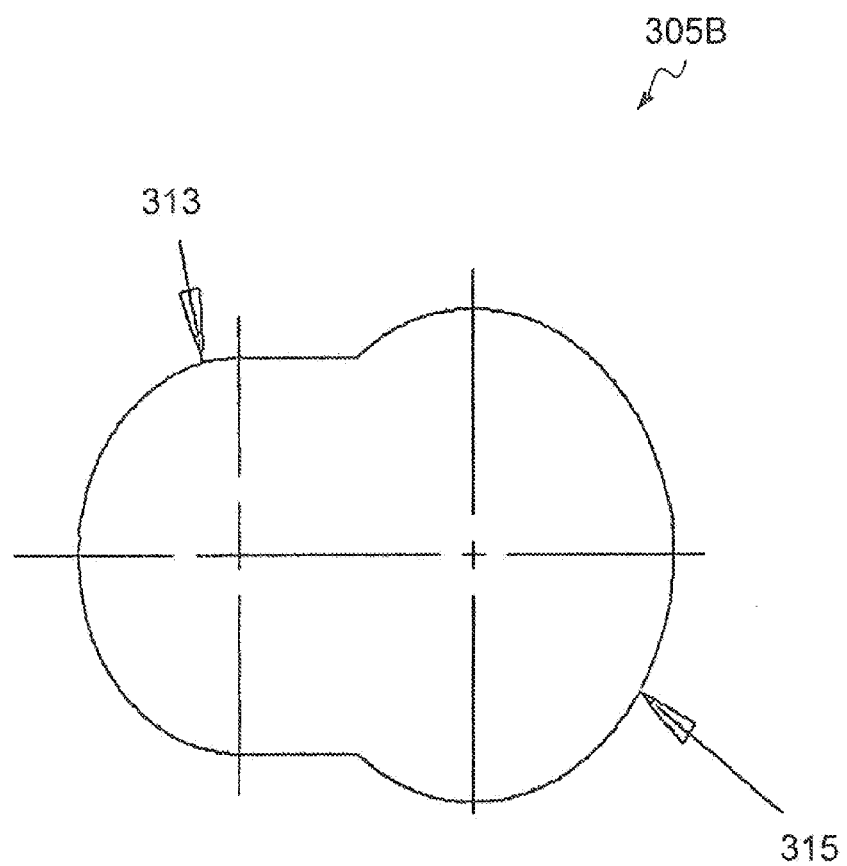
FIG. 3C illustrates a nipple hole of the lens of the flip-to-wear eye shield according to the alternate embodiment of the invention of FIG. 3B.
Figure 4:
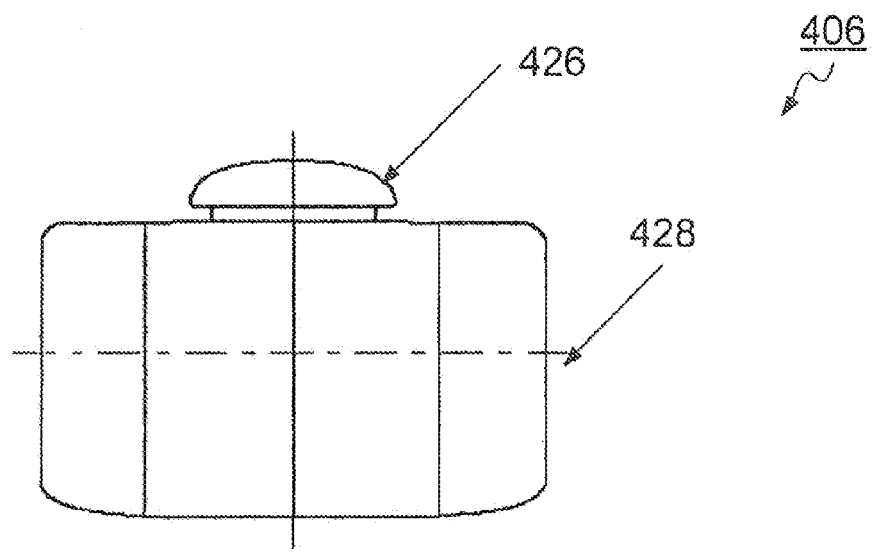
FIG. 4 illustrates a nipple coupled with a hinge of an exemplary flip-to-wear eye shield according to one embodiment of the invention.

FIG. 3A illustrates a lens for a flip-to-wear disposable eye shield according to an exemplary embodiment of the invention. In the illustrated embodiment, lens 304 includes notch 324 for resting on or extending slightly above the bridge of a user's nose. The distance from the top edge of the lens 304A to the top of notch 324 is given by dimension 307. The distance from the top edge of the lens 304A to the bottom edge is given by dimension 309. Lens 304A further includes notches 310, and nipple holes 305A. As discussed above, notches 310 are designed to align with the connective mechanisms (such as bends) 208 of FIG. 2 so that the notches 310 may be locked into the bends 208 when the eye shields are in the fully assembled position ready for wearing and use. In this embodiment, nipple holes 305A are used as a mechanism to connect the lens 304A to the frame, such as frame 102 of FIG. 1, using hinges such as hinges 106. The nipple holes 305A are round-shaped holes cut through lens 304A. The round nipple holes 305A of lens 304A may be connected with the frame using one or more nipples such as the nipples illustrated in FIG. 4 and FIG. 5. Referring momentarily to FIG. 4, which illustrates a nipple coupled with a hinge of an exemplary flip-to-wear eye shield according to one embodiment of the invention. It is noted that the hinge 406 includes a nipple 426 and housing 428. The housing 428 is for connection with the frame of the exemplary eye shield to be discussed below. The nipple 426 is for connection with the lens using the nipple hole 305A illustrated in FIG. 3A. In this embodiment, the lens is connected to the hinge 406 by inserting each nipple 426 into the nipple holes 305A. This may be accomplished using a nipple 426 that is slightly larger than the nipple holes 305A. In such a case, the nipple 426 may be secured to the lens 304A by poking each nipple 426 through the nipple holes 305A. It should be pointed out that this connection mechanism is given by way of example and not of limitation as any number of mechanisms known in the art may be used to couple the lens 304 with the frame using the hinges. For example, FIG. 3B illustrates a lens for a flip-to-wear eye shield according to the alternate embodiment of the invention. In FIG. 3B, lens 304B includes notches 310 and nipple holes 305B. The nipple holes 305B are dual-sized holes cut through lens 304A such as those shown in FIG. 3C, which illustrates a nipple hole of the lens of the flip-to-wear eye shield according to the alternate embodiment of the invention of FIG. 3B. In FIG. 3C nipple hole 305B is a dual-sized hole having a larger radius 315 and a smaller radius 313. The nipple hole 305B is used as an alternate mechanism for connecting the lens 304B with the hinge of the frame using a nipple such as the nipples illustrated in FIG. 4 and FIG. 5. In this embodiment, the lens is secured to the hinge 406 by inserting the nipple 426 into the nipple hole 305B. This may be accomplished using the larger radius of the dual-sized nipple hole 305B for inserting the nipple 426 and then sliding the nipple 426 into the smaller radius of the dual-sized nipple hole 305B securing the nipple 426 to the lens. Once again, this is given by way of example and not of limitation as any mechanism of securing the hinge 406 to the lens is contemplated within the teachings of this description.

Figure 5:
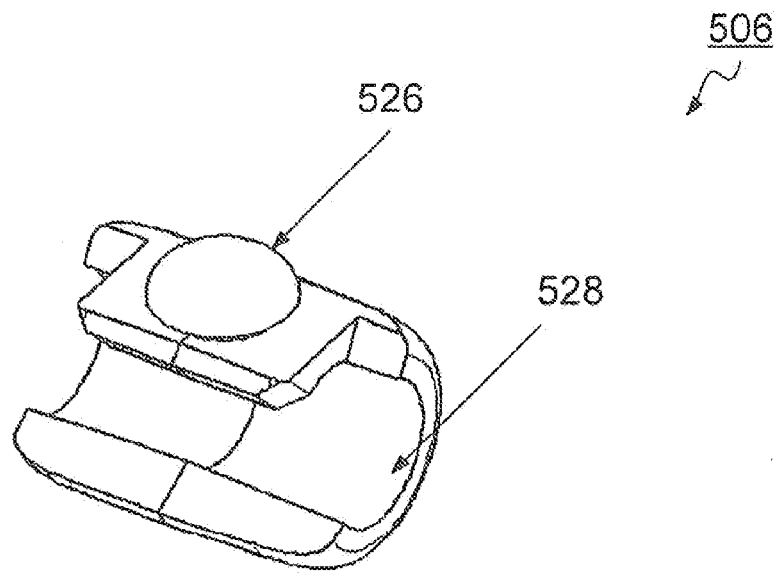
FIG. 5 illustrates another angle of the nipple coupled with a hinge of the exemplary flip-to-wear eye shield according to the embodiment illustrated in FIG. 4.
Figure 6:
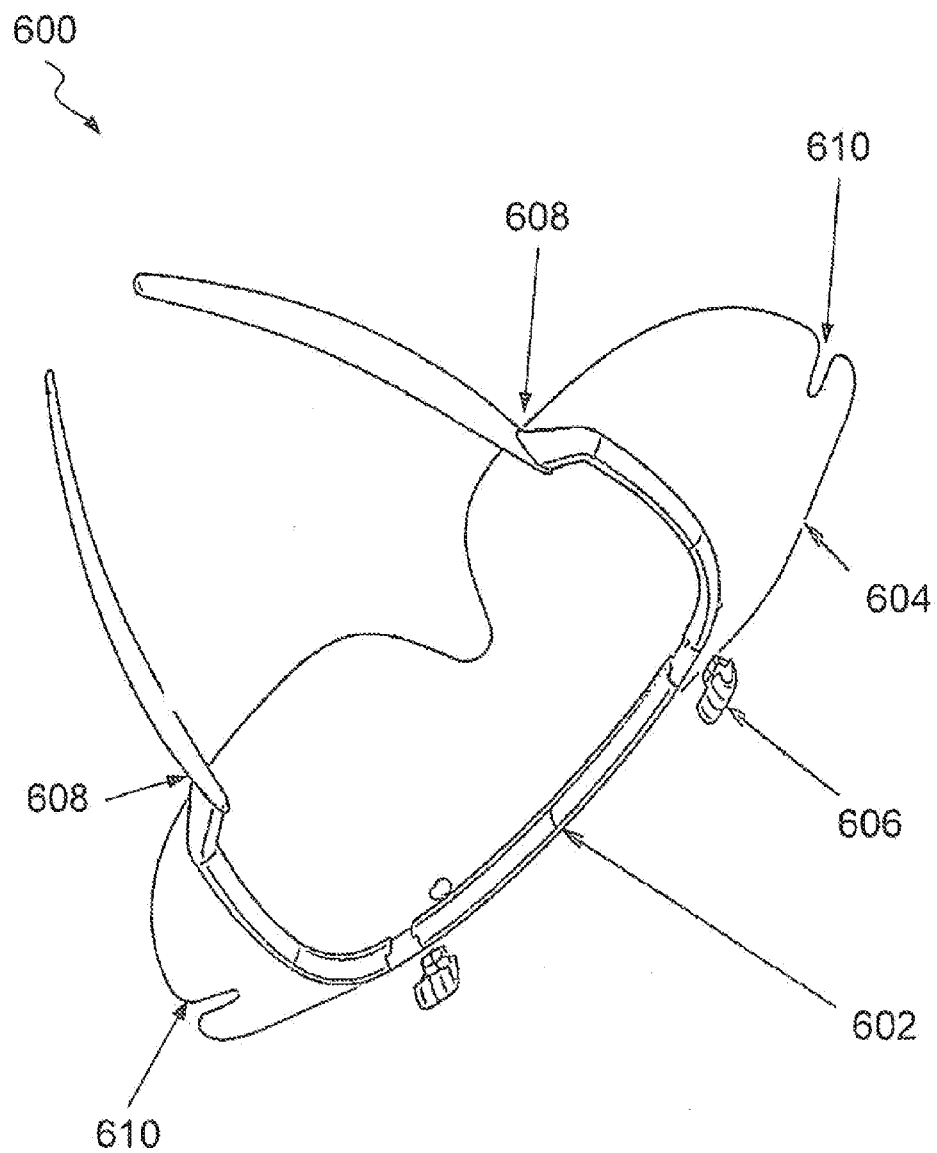
FIG. 6 illustrates an exemplary flip-to-wear eye shield in the substantially flat position according to one embodiment of the invention.
Figure 10:
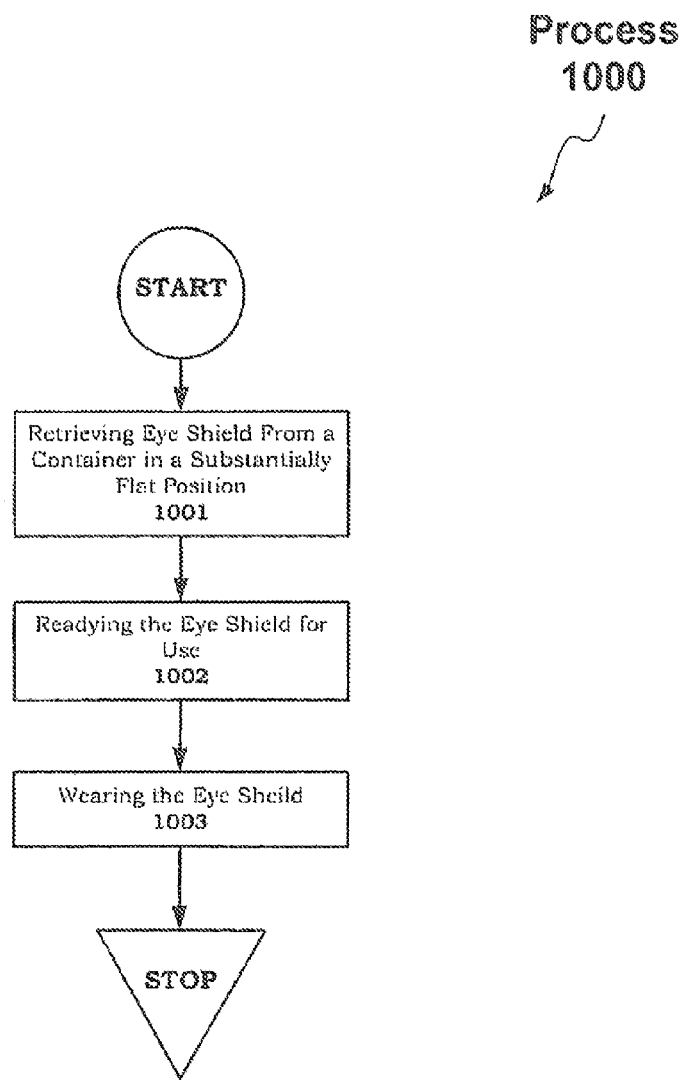
FIG. 10 illustrates a flow diagram of a process for deploying a flip-to-wear eye shield from its first substantially flat position into the position readied for use according to an exemplary embodiment of the invention.

FIG. 5 illustrates another angle of the nipple coupled with a hinge of the exemplary flip-to-wear eye shield according to the embodiment illustrated in FIG. 4. In the illustrated embodiment, hinge 506 includes nipple 526 for connection with the nipple holes of the lens of the exemplary eye shield as discussed above and housing 528 for connection with the frame of the exemplary eye shield. The housing 528 is configured in a semi-circular shape to facilitate attachment of the hinge 506 to the frame of the eye shield and to allow the hinge 506 to pivot up and down while attached to the frame. (Note that the hinge is wider on one side than on the other so that the range of motion of the hinge may be stopped when the lens is in the correct position). This is further shown in FIG. 6 which illustrates an exemplary flip-to-wear eye shield in the substantially flat position according to one embodiment of the invention. Eye shield 600 includes hinges 606 that are attachable to the frame 602 and the lens 604 in a pivoting relationship. In one embodiment, the body of the hinges 606 may be attached to the frame 602 and the nipple of the hinges 606 may be attached to the lens 604 as described above. The hinges 606 may be fixed, or detachable and replaceable. In FIG. 6 the eye shield 600 is shown in the substantially flat position. Eye shield 600 may be readied for use by pivoting the eye shield from the substantially flat position to a fully assembled position readied for use by pushing the lens 604 down so that it rotates inside the frame 602, pivoting the lens 604 with respect to the frame 602 on the hinges 606 until the notches 610 on the lens 604 are locked into position onto the connective mechanisms 608. This process is described in conjunction with FIG. 10 which illustrates a flow diagram of a process for deploying the flip-to-wear eye shield into the position readied for use according to an exemplary embodiment of the invention. Process 1000 begins at operation 1001 where the eye shield is retrieved from a container in the substantially flat position. Method 1000 proceeds with operation 1002 where the eye shield is readied for use. This is accomplished by pivoting the lens 604 on hinges 606 down inside the frame 602 until the hinges 606 stop rotating on the frame 602 and the notches 610 on the lens 604 are engaged with and locked into position into the connective mechanisms 608 on frame 602. The eye shield is then placed on a user's face for use at operation 1003. This completes exemplary process 1000.

Figure 7:
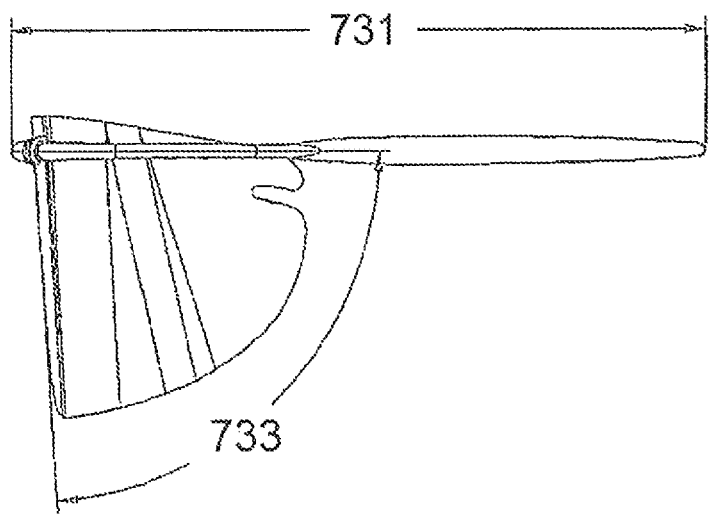
FIG. 7 illustrates a side view of the flip-to-wear eye shield in a position readied for use according to an exemplary embodiment of the invention.

FIG. 7 illustrates a side view of the flip-to-wear eye shield in a position readied for use according to an exemplary embodiment of the invention. In this side view the length of the exemplary eye shield is shown as dimension 731 with an angle 733 between the lens and the frame when eye shield is in the fully assembled position ready for use.

Figure 8:
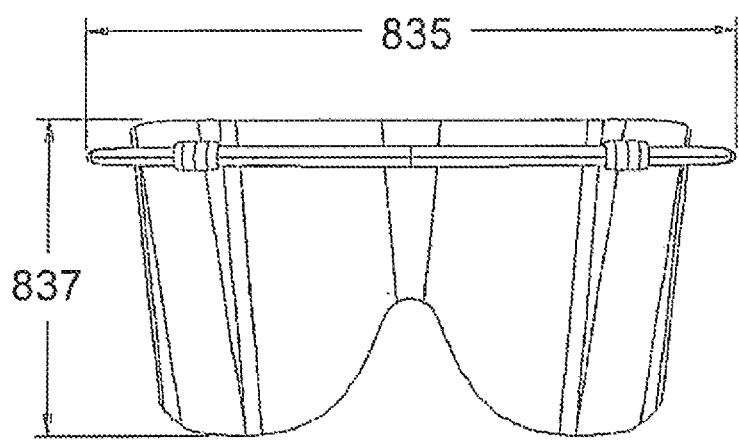
FIG. 8 illustrates a front view of the flip-to-wear eye shield in the position readied for use according to an exemplary embodiment of the invention.

FIG. 8 illustrates a front view of the flip-to-wear eye shield in the position readied for use according to an exemplary embodiment of the invention. In this front view the width of the exemplary eye shield is shown as dimension 835 and the height of the exemplary eye shield is shown as dimension 837.

Figure 9:
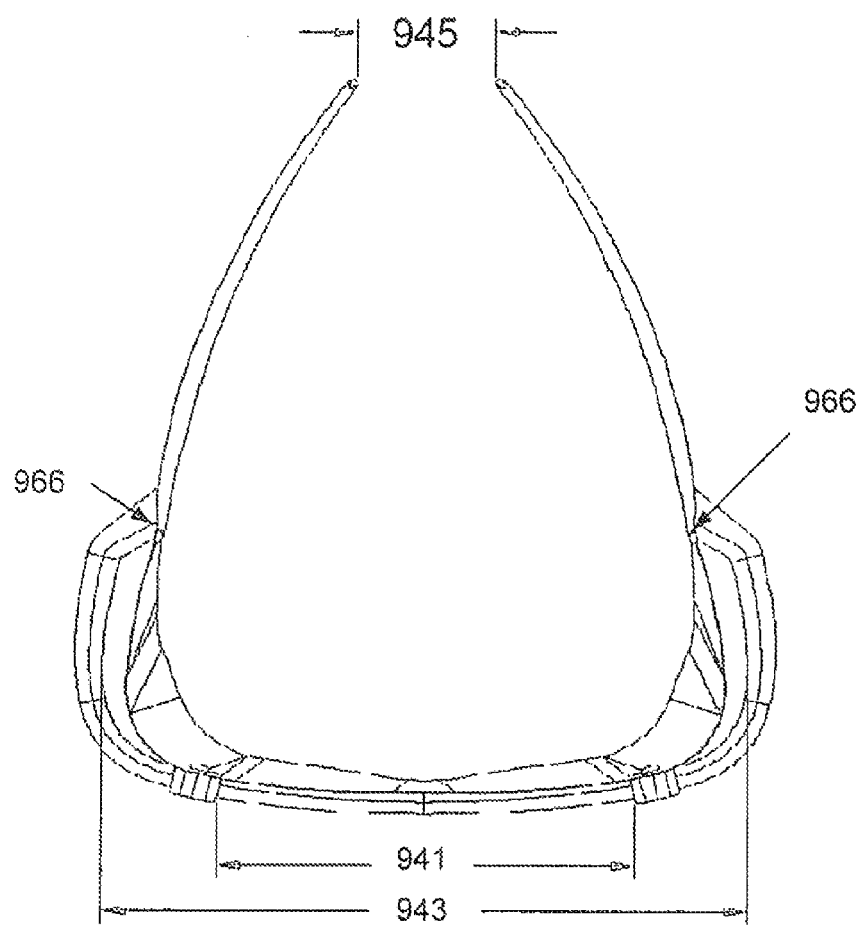
FIG. 9 illustrates a top view of the flip-to-wear eye shield in the position readied for use according to an exemplary embodiment of the invention.

FIG. 9 illustrates a top view of the flip-to-wear eye shield in the position readied for use according to an exemplary embodiment of the invention. In this top view the distance between the hinges, such as hinges 106 of FIG. 1, is given by dimension 941. This distance corresponds to the approximate distance so that each hinge is located directly above the eyes of the average user. In addition, the distance between areas 966 of the frame of the exemplary eye shield is shown as dimension 943 designed to extend beyond the area of the temples of the average user. The distance between the opposite ends, such as opposite ends 212 of FIG. 2, is given by dimension 945.

Figure 11A:
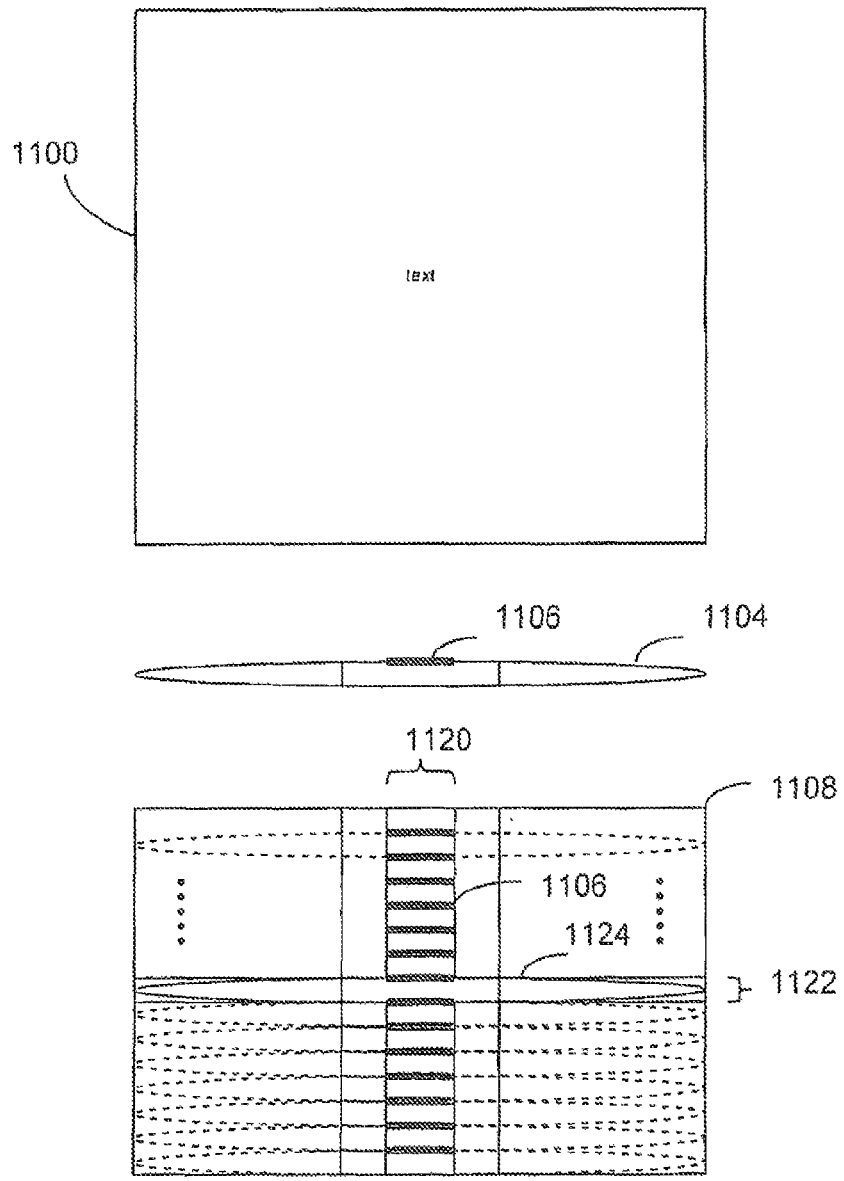
FIG. 11A illustrates an example of a dispenser box holding packages of flip-to-wear eye shields in the substantially flat position according to one embodiment of the invention.

FIG. 11A illustrates an example of a dispenser box holding packages of flip-to-wear eye shields in the substantially flat position according to one embodiment of the invention. The eye shields may be stored in and dispensed from a dispenser box such as dispenser box 1100 in the figure. In one embodiment, the dispenser box 1100 is a narrow, thin square box with a top flap which opens to dispense the exemplary eye shields. In this case, the exemplary eye shields are efficiently and inexpensively stored in the substantially flat position. In an alternative embodiment, the exemplary eye shields may be stored as shown at the bottom of FIG. 11A. In this case, a tap 1102 may be attached to a package containing each exemplary eye shield in a wrap in order to aid a user in pulling the package out of the dispenser box 1100. A top view of the package 1104 shows the attached tap 1106 on top. A top view of the dispenser box 1108 shows a group of packages 1124 contained inside the dispenser box 1108, which has an opening 1120 for taps 1106 and another opening 1122 for the package to be pulled out on the tap 1120. In one embodiment, the openings 1120 and 1122 may be detachable using perforated lines on a paper dispenser box 1108 for initial use. (Not going this route with the box.)

Figure 11B:
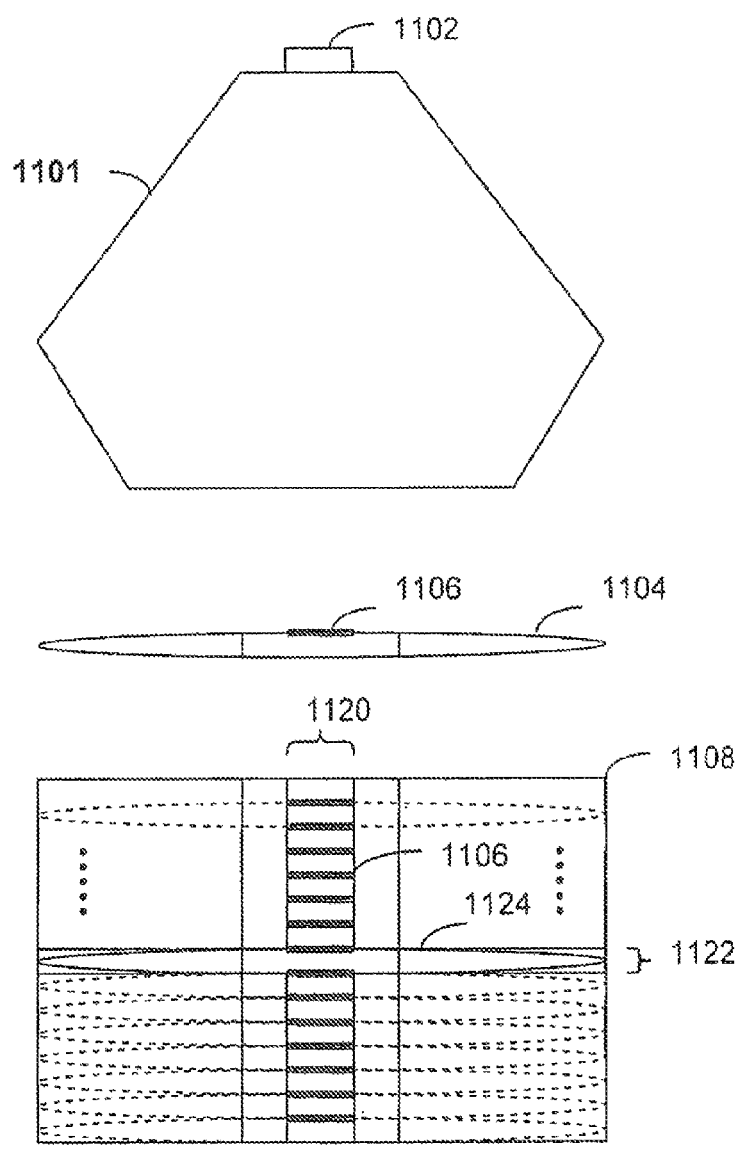
FIG. 11B illustrates an alternative configuration for the dispenser box holding packages of flip-to-wear eye shields in the substantially flat position according to the illustrated embodiment of FIG. 11A.

FIG. 11B illustrates an alternative configuration for the dispenser box holding packages of flip-to-wear eye shields in the substantially flat position according to the illustrated embodiment of FIG. 11A. In this case, the eye shields may be stored in and dispensed from a dispenser box such as dispenser box 1101 with a shape that follows the shape of the exemplary flip-to-wear eye shield. This dispenser box 1101 may also include a tap 1102 attached to each package in a wrap to aid a user in pulling the package out of the dispenser box 1101.

Figure 12:
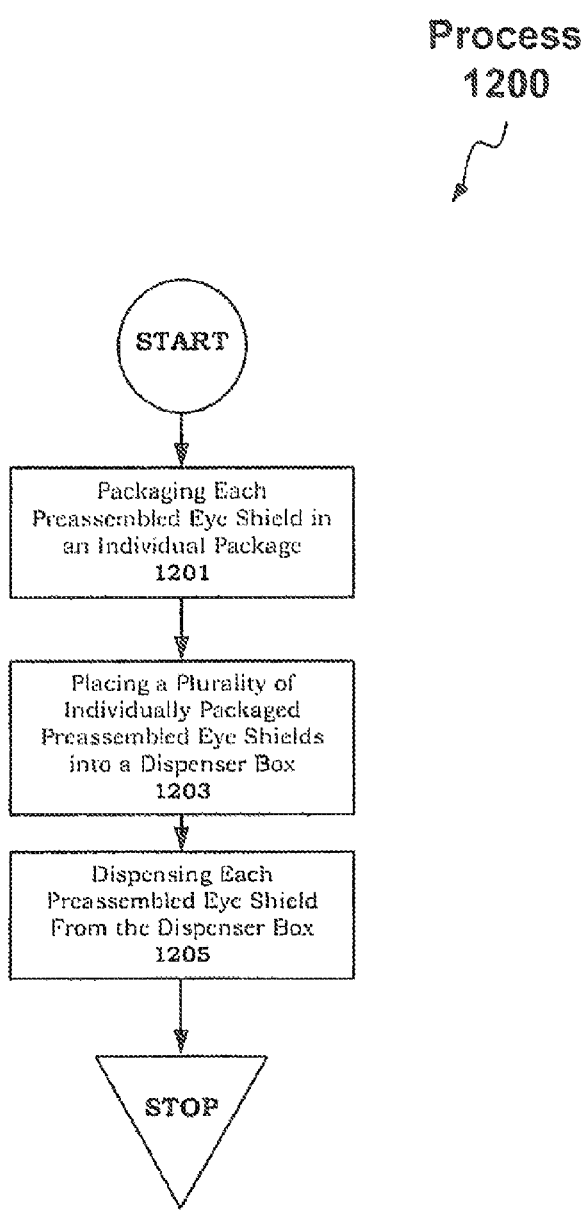
FIG. 12 illustrates a flow diagram depicting a process for dispensing a flip-to-wear eye shield according to an exemplary embodiment of the invention.

FIG. 12 illustrates a flow diagram depicting a process for dispensing a flip-to-wear eye shield according to an exemplary embodiment of the invention. In process 1202 each preassembled flip-to-wear eye shield is individually packaged. In the process 1203 the packages containing the flip-to-wear eye shields are placed in a dispenser box. In the process 1206 one eye shield at a time is dispensed by pulling out the flat package from the dispenser box. In one embodiment, the package has a tap attached to wrap around the package that can be used when the package is pulled out. The tap and wrap is arranged in such a way that when one package is pulled out by the tap, the next package tap and wrap moves to a position to be pulled out next time, thus saving a user the effort to find and drag the next tap attached to the next package to a position aligned to the opening of the disperser box to pull out the package. Other embodiments do not include a tap as described above.

Throughout the foregoing specification, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. When a particular feature, structure, or characteristic is described in connection with an embodiment, it is submitted that it is within the knowledge of one skilled in the art to bring about such a feature, structure, or characteristic in connection with other embodiments whether or not explicitly described. Various changes may be made in the structure and embodiments shown herein without departing from the principles of the invention. Further, features of the embodiments shown in various figures may be employed in combination with embodiments shown in other figures.

In the description as set forth above and claims, the terms "coupled" and "connected," along with their derivatives, may be used. It should be understood that these terms are not intended to be synonymous with each other. Rather, in particular embodiments, "connected" is used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Throughout the foregoing description, for the purposes of explanation, numerous specific details were set forth in order to provide a thorough understanding of the invention. It will be apparent, however, to one skilled in the art that the invention may be practiced without some of these specific details.

Accordingly, the scope and spirit of the invention should be judged in terms of the claims which follow as well as the legal equivalents thereof.

What is claimed is:

1. An eye shield, comprising:
    a frame for supporting the eye shield upon a user, the frame including a forehead portion that aligns with a forehead of the user and a pair of side extensions that extend in a rearward direction from the forehead portion so that the forehead portion and the side extensions are aligned in a plane;
    a hinge arranged upon the forehead portion of the frame; and
    a lens that is flexible and mounted to the hinge, the lens arranged for movement about multiple axes with respect to the frame such that the lens moves from a flat position in which the lens lies in the plane to conform to a shape of the frame by pivoting about the hinge and the forehead portion of the frame and bowing relative to the side extensions of the frame.

2. The eye shield of claim 1, wherein the lens and frame define cooperating notches and projections for securing outer portions of the lens to the side extensions of the frame.

3. The eye shield of claim 2, wherein the notches and projections engage each other at a location on the frame that is rearward of bowed segments of the lens defined at locations at the lens bowing relative to the side extensions of the frame.

4. The eye shield of claim 2, wherein the lens defines a pair of opposing outer portions, side portions, and a pair of notches that extend into the outer portions.

5. The eye shield of claim 4, wherein each of the notches includes an opening that faces outwardly away from the remainder of the lens.

6. An eye shield, comprising:
    a frame for supporting the eye shield upon a user, the frame including a forehead portion that aligns with a forehead of the user and a pair of side extensions that extend in a rearward direction from the forehead portion so that the forehead portion and the side extensions are aligned in a plane;
    a pair of hinges spaced from each other and arranged upon the forehead portion of the frame, each of the hinges including a segment that extends outwardly in a transverse direction from the forehead portion of the frame; and
    a lens arranged for movement with respect to the frame and including a pair of openings arranged at an upper section of the lens for removably engaging the segments of the hinges that extend outwardly to secure the lens to the frame.

7. The eye shield of claim 6, wherein each of the segments of the hinges that extend outwardly defines a nipple that extends away from the frame.

* * * * *